United States Patent [19]

Satta et al.

[11] Patent Number: 4,655,892
[45] Date of Patent: Apr. 7, 1987

[54] OXYGEN SENSOR AND PROCESS FOR PRODUCING SAME

[75] Inventors: Kozo Satta; Hideo Hasegawa; Mareo Kimura, all of Aichi, Japan

[73] Assignee: Kabushiki Kaisha Toyota Chuo Kenkyusho, Aichi, Japan

[21] Appl. No.: 758,376

[22] Filed: Jul. 24, 1985

[30] Foreign Application Priority Data

Jul. 24, 1984 [JP] Japan .................. 59-153775

[51] Int. Cl.$^4$ .................. C23C 14/18; B05D 5/00; B05D 3/02; G01N 27/46
[52] U.S. Cl. .................. 204/192.15; 204/421; 204/424; 204/192.12; 427/124; 427/125; 427/372.2; 427/377; 427/380; 427/383.5
[58] Field of Search .................. 204/1 S, 421–429; 427/124, 125, 372.2, 377, 379, 380, 383.1, 383.3, 383.5

[56] References Cited

U.S. PATENT DOCUMENTS

| | | | |
|---|---|---|---|
| 4,186,071 | 1/1980 | Romine et al. | 204/427 |
| 4,199,425 | 4/1980 | Sinkevitch | 204/429 |
| 4,225,559 | 9/1980 | Achari et al. | 204/424 |
| 4,253,934 | 3/1981 | Berg et al. | 204/424 |
| 4,294,668 | 10/1981 | Young | 204/424 |

FOREIGN PATENT DOCUMENTS 1462639  1/1977  United Kingdom .............. 204/429

Primary Examiner—T. Tung
Attorney, Agent, or Firm—Finnegan, Henderson, Farabow, Garrett & Dunner

[57] ABSTRACT

An oxygen sensor for sensing the oxygen content of an exhaust gas from an automotive engine and a process for producing the same, which sensor is less sensitive to lead poisoning than conventional sensors. In the inventive sensor, a first platinum electrode is formed on the side of a solid electrolyte body exposed to the gas to be detected, and a second electrode is formed on the other side of the electrolyte body. The first electrode comprises a platinum layer and a layer of at least one of rhodium and palladium. Preferably, the layer of rhodium or palladium has a thickness of 10 to 5,000 Å.

9 Claims, 7 Drawing Figures (×2000)

(×2000)

(×2000)

(×2000)

OXYGEN SENSOR AND PROCESS FOR PRODUCING SAME

BACKGROUND OF THE INVENTION

The present invention relates to a sensor for detecting the concentration of oxygen in exhaust gas emitted from an internal combustion engine of an automobile or other vehicle. The present invention also relates to a process for producing such an oxygen sensor.

Most modern automobiles are designed so that the composition of exhaust gas from engines is kept constant by monitoring the concentration of oxygen in the exhaust gas. The data obtained from such monitoring on oxygen concentration is fed back to a fuel injection system, which in response controls the amount of fuel jetted into the engine so as to maintain a cleaner exhaust gas.

The concentration of oxygen in the exhaust gas is conventionally measured by a device called an oxygen sensor. The prior art oxygen sensor has a solid electrolyte (e.g., zirconia, $ZrO_2$) body as the base material and includes electrodes, such as those made of platinum, on both sides of the base, with a porous ceramic protective layer such as one made of magnesia-alumina ($MgO.Al_2O_3$) spinel being provided on the electrode surface which is in contact with oxygen gas.

Such a prior art oxygen sensor, however, experiences a gradual drop in sensing performance during service. This is believed due to lead poisoning of the electrodes wherein lead in the exhaust gas from the fuel reacts with the sensor electrodes to produce a condensation layer that deprives the electrodes of electrical conductivity.

In order to prevent such lead poisoning of the oxygen sensor, attempts have been made to use thicker electrodes. However, as the thickness of the electrode is increased, the response time, which is one important parameter of the sensor, is increased unless the sensor is subjected to complicated treatments such as aging with an actual exhaust gas.

SUMMARY OF THE INVENTION

One object, therefore, of the present invention is to provide an oxygen sensor that is less sensitive to lead poisoning and which can be used for an extended period without experiencing any significant decrement in response characteristics or other sensor parameters.

Another object of the invention is to provide a process for producing such an oxygen sensor.

In accordance with one aspect of the present invention, an oxygen sensor is provided which has a first platinum electrode formed on that side of a solid electrolyte body which is exposed to a gas of interest, and a second electrode formed on the other side of the electrolyte body. This sensor is characterized in that the surface of the first electrode is provided with a layer made of either rhodium or palladium or both.

In accordance with another aspect of the present invention, a process for producing an oxygen sensor is provided in which a first platinum electrode is formed on that side of a solid electrolyte body which is exposed to a gas of interest, and a second electrode is formed on the other side of the electrolyte body. This process is characterized in that a first electrode metal layer made of both platinum and either rhodium or palladium or both is formed on the side of the platinum layer exposed to this gas, and the first electrode metal layer so formed is first subjected to oxidation, then to reduction, thereby forming the first electrode composed of the platinum layer and a layer of either rhodium or palladium or both.

DESCRIPTION OF THE PREFERRED EMBODIMENTS

The present invention is hereunder described by reference to the accompanying drawings.

Figure 1:
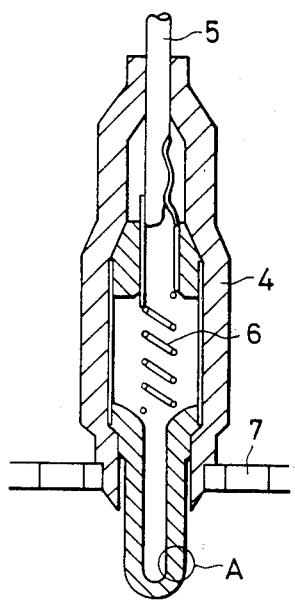
FIG. 1 is a schematic section showing an embodiment of an oxygen sensor in accordance with the present invention.
Figure 2:
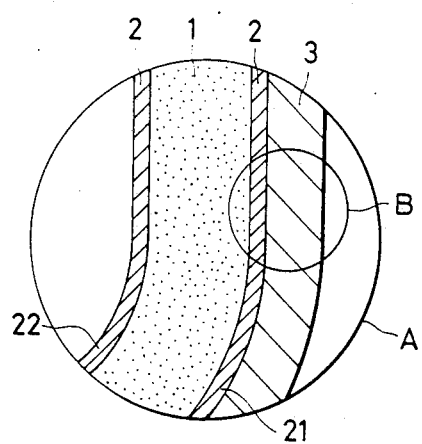
FIG. 2 shows a portion A of FIG. 1 on an enlarged scale.
Figure 3:
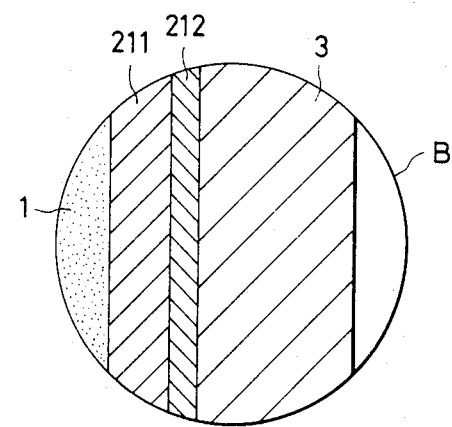
FIG. 3 shows a portion B of FIG. 2 on an enlarged scale.

FIG. 1 is a schematic cross section showing an oxygen sensor in accordance with one embodiment of the present invention. FIG. 2 shows a portion A of FIG. 1 on an enlarged scale. FIG. 3 shows a portion B of FIG. 2 on an enlarged scale. It should be understood that the construction of the oxygen sensor in accordance with the present invention is by no means limited to that shown in FIGS. 1 to 3.

Referring to FIGS. 1 to 3, a solid electrolyte body indicated at 1 is made of zirconia, thoria, ceria, ceria-lanthania, ceria-thoria-lanthania, bismuth oxide or any other material that is commonly used as the material for the solid electrolyte body of an oxygen sensor. Preferred solid electrolyte materials are zirconia ($ZrO_2$) doped with oxides of elements such as yttrium (Y), calcium (Ca), magnesium (Mg), ytterbium (Yb), cerium (Ce), scandium (Sc), lanthanum (La) and strontium (Sr).

As shown in FIG. 1, the solid electrolyte body 1 is of a tubular form with the sensing ends closed, and electrode means 2 are formed on both surfaces of the electrolyte body 1. As shown in FIG. 2, a first electrode 21 is formed on that side of the electrolyte body 1 which is exposed to a gas of interest, whereas a second electrode 22 is formed on the other side of the electrolyte body 1. The first electrode 21 is made of platinum, and it is preferred that the second electrode 22 also be made of platinum to ensure stable electrical conductivity. The second electrode 22 may also be formed of other noble metals such as palladium. In accordance with the present invention, the platinum layer forming the first electrode 21 is overlaid with a layer made of either rhodium or palladium or both. The presence of either rhodium or palladium or both on the surface of the electrode 21 prevents it from being poisoned by lead from the fuel.

The first electrode 21 may be formed by the following procedure. First, an electrode metal layer made of both platinum and either rhodium or palladium or both is formed on one surface of the solid electrolyte body. This first electrode metal layer may be formed by spraying or printing a paste of a mixture of platinum and either rhodium or palladium or both on that surface of the solid electrolyte body 1 which is to be exposed to a gas of interest, and the applied layer is fired. Alternatively, both platinum and either rhodium or palladium or both are formed on that surface of the electrolyte body 1, which is exposed to a gas to be detected, by sputtering, evaporation or plating. The amount of rhodium and/or palladium to be incorporated in the first electrode metal layer is preferably in the range of 0.1 to 50 wt% of the total weight of that layer. If the proportion of rhodium and/or palladium is less than 0.1 wt% of the first electrode metal layer, the desired prevention of lead poisoning may not be realized. If the proportion is more than 50 wt% of the metal layer, no commensurate increase in the ability to prevent lead poisoning is obtained and the material cost is simply increased.

The first electrode metal layer thus formed is then subjected to oxidation and reduction treatments. As a result of these treatments, either the rhodium or the palladium or both in the metal layer are concentrated in the surface layer, producing an electrode of dual structure wherein the platinum layer is overlaid with the layer of either rhodium or palladium or both. When both rhodium and palladium are incorporated in the first electrode metal layer, a three-layered electrode may form as a result of the oxidation and reduction treatments, wherein the platinum layer is overlaid first with a rhodium layer, then with a palladium layer.

In the oxidation treatment, the first electrode metal layer formed on one surface of the solid electrolyte body 1 is heated in an oxidizing atmosphere such as oxygen gas. The heating temperature is preferably in the range of 600° to 900° C. At temperatures lower than 600° C., rhodium and/or palladium will not be easily concentrated on the electrode surface. At temperatures higher than 900° C., such adverse effects as the formation of a condensed Pt layer on the entire electrode surface may occur. The duration of the oxidation treatment will vary with the thickness of the electrode to be formed, and is generally in the range of from 5 minutes to 3 hours.

In the reduction treatment, the oxidized first electrode metal layer is heated in a reducing atmosphere such as hydrogen gas. The heating is preferably performed at a temperature in the range of 100° to 200° C. for a duration that ranges from 5 minutes to 1 hour. As a result of this reduction treatment, the rhodium or palladium or both which are concentrated as oxides in the electrode surfaces are reduced to their respective elemental forms. Additionally, fine pores are formed in the electrode, causing a further improvment in the response characteristics of the sensor.

The second electrode is subsequently formed by any of the methods conventionally employed. If desired, the method used for making the first electrode may be applied to form a second electrode of a dual structure.

The result of the oxidation and reduction treatments is shown in FIG. 3, wherein the first electrode 21 is formed on that side of the solid electrolyte body 1 which is exposed to a gas of interest and the second electrode 22 is formed on the other side of the electrolyte body, with the first electrode 21 being composed of a platinum layer 211 overlaid with a layer 212 made of rhodium and/or palladium.

The platinum layer 211 of the first electrode 21 preferably has a thickness of 0.1 to 1.5 microns. If the thickness is below 0.1 micron, the electrode may not have adequate heat resistance, and if the thickness is greater than 1.5 microns, the response of the electrode as a sensor is reduced. The layer 212 made of rhodium and/or palladium preferably has a thickness of 10 to 5,000 Å and more preferably 200 to 500 Å. If the thickness is smaller than 10 Å, the desired ability to prevent lead poisoning may not be obtained, and if the thickness exceeds 5,000 Å, the response of the electrode as a sensor is reduced and the material cost is increased.

A protective layer 3 may be formed on the surface of the first electrode 21 to prevent deposition of combustion products present in the exhaust gas. The protective layer may be formed of magnesia-alumina ($MgO.Al_2O_3$) spinel or alumina ($Al_2O_3$).

The oxygen sensor thus fabricated in accordance with the present invention is mounted in a holder 4, as shown in FIG. 1, for use in sensing the exhaust gas emitted from an automobile engine. Any electrical signal detected by the oxygen sensor is transmitted to an external circuit through a lead wire 5 for determining the concentration of oxygen in the exhaust gas. In FIG. 1, reference numeral 6 indicates a spring, and 7 is a mounting flange. The present invention is also applicable to the so called lean sensor besides the oxygen sensor illustrated in FIG. 1.

In accordance with the first aspect of the present invention, there is provided a durable oxygen sensor that is protected from electrode poisoning by lead in a gas of interest. A plausible explanation for this advantage is as follows: the layer of rhodium and/or palladium formed on the surface of an electrode exposed to the gas of interest reacts with the lead from the fuel and prevents the penetration of lead into the electrode so that platinum (the active material for the electrode) will not be deteriorated by lead poisoning. Additionally, the oxygen sensor in accordance with the first aspect of the present invention has stable response characteristics and can be used for a prolonged period without experiencing a drop in its capability of sensing the oxygen concentration.

In accordance with the second aspect of the present invention, a process for producing the oxygen sensor described above having good characteristics is provided. According to this process, an electrode unit having improved resistance to lead poisoning is formed by the simple treatments of oxidation and reduction. Since the reduction treatment produces fine pores in the electrode unit, the resulting oxygen sensor has a quicker response. Conventionally, the response characteristics of oxygen sensors are improved by prolonged aging with the actual exhaust gas at elevated temperatures, but this is no longer necessary for the oxygen sensor produced by the second aspect of the present invention.

The following Experiments and Examples are provided for further illustration of the present invention.

EXPERIMENT 1

On a zirconia substrate forming a solid electrolyte body was formed a first electrode metal layer (2,000 Å thick) by sputtering an alloy of platinum (Pt) and 10 wt% rhodium (Rh) (percentages noted hereunder indicate weight percentages). The resulting electrode layer was subjected to an oxidation treatment wherein it was heated in oxygen gas at 600° C. for 1 hour. Subsequently, the oxidized metal layer was subjected to a reduction treatment, wherein it was heated in hydrogen gas at 150° C. for 30 minutes. By these procedures, the first electrode portion of an oxygen sensor in accordance with the present invention was formed (Sample No. 1).

Two comparative electrode samples were prepared: a Pt layer with a thickness of 2,000 Å was formed on a zirconia substrate by sputtering, and a layer of Pt-10%

Rh alloy (thickness: 2,000 Å) was formed on a zirconia substrate by sputtering. The resulting layers were immediately used as Samples Nos. C1 and C2 without subjecting them to oxidation or reduction treatment.

The structure of each of the three electrode samples was observed by a scanning electron microscope (SEM) and an ion microprobe mass analyzer (IMMA). The electrode portion of Sample No. 1 had a dual structure consisting of a Pt layer about 1,800 Å thick overlaid with a Rh-concentrated layer about 200 Å thick. A number of fine pores were found in the electrode. Samples Nos. C1 and C2 had a homogeneous monolayer structure with no fine pores present.

In order to check for the resistance to lead poisoning, the three electrode samples were subjected to the following test: a Pb layer 500 Å thick was sputtered onto the surface of each sample, which was then heated in a reducing atmosphere ($H_2$ gas) at 900° C. for 1 hr. The heating conditions used in this test were more severe than the conditions of actual use for oxygen sensors in the exhaust gas emitted from automobile engines.

After the poisoning test, the surface of the electrode of each sample was observed by an SEM. SEM micrographs showing the metallurgical structures of the respective electrodes are reproduced in FIG. 4 (Sample No. 1), FIG. 5 (Sample No. C1) and FIG. 6 (Sample No. C2) at a magnification of 2,000.

Figure 4:
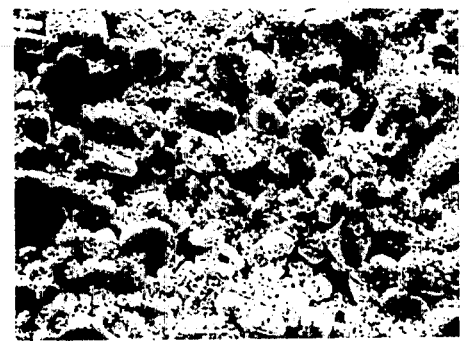
FIGS. 4 and 7 are SEM micrographs showing the surface structures of electrode surfaces for Sample Nos. 1 and 2 that were subjected to a Pb poisoning test.
Figure 5:
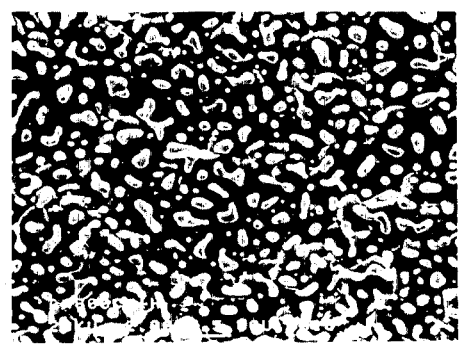
FIGS. 5 and 6 are SEM micrographs showing the surface structures of electrode surfaces for Samples Nos. C1 and C2 after the Pb poisoning test.
Figure 6:
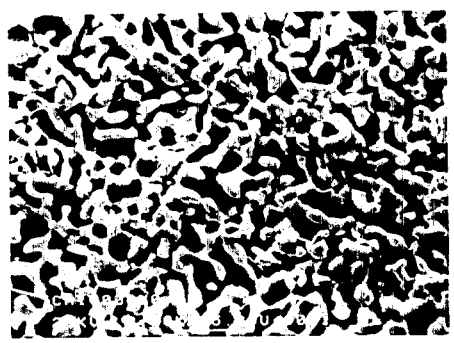

As FIG. 5 shows, the electrode of Sample No. C1 was extensively poisoned by Pb, which condensed to such an extent that large islands of Pt grains formed. As FIG. 6 shows, large pores occurred in the electrode of Sample No. C2 and it was nonconductive in some areas. On the other hand, as shown in FIG. 4, neither large pores nor nonconductive parts occurred in the electrode of Sample No. 1, which hence performed satisfactorily as an electrode, maintaining good conduction throughout its surface area or bulk. It is therefore clear that the oxygen sensor in accordance with the present invention has high resistance to lead poisoning.

The materials of the electrodes of the three samples tested and the results of the Pb poisoning test are summarized in Table 1 below:

TABLE 1

| Sample No. | Electrode layer composition | thickness Å | Oxidation reduction treatments | Resistance to Pb poisoning |
|---|---|---|---|---|
| 1 | Pt-10% Rh | 2,000 | yes | good |
| C1 | Pt | 2,000 | no | poor |
| C2 | Pt-10% Rh | 2,000 | no | poor |

EXPERIMENT 2

On a zirconia substrate forming a solid electrolyte body was formed a first electrode metal layer (2,000 Å thick) by sputtering an alloy of platinum (Pt) and 10% palladium (Pd). The resulting electrode layer was subjected to oxidation and reduction treatments as in Experiment 1, thereby forming the first electrode portion of an oxygen sensor in accordance with the present invention (Sample No. 2).

The structure of the electrode of Sample No. 2 was observed by SEM and IMMA. It had a dual structure consisting of a Pt layer about 1,800 Å thick that was overlaid with a Pd-concentrated layer about 200 Å thick. This electrode was tested for its resistance to lead poisoning as in Experiment 1 and the surface of the heated electrode was observed by SEM. A SEM micrograph showing the metallurgical structure of the electrode is reproduced in FIG. 7 at a magnification of 2,000.

Figure 7:
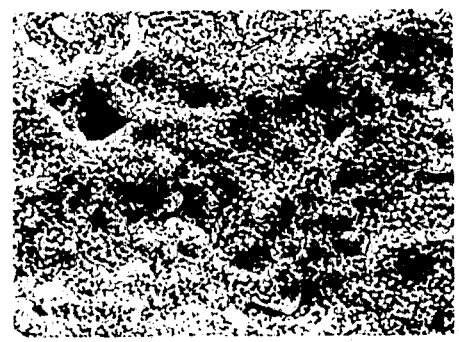

As one can readily see from FIG. 7, the electrode prepared in accordance with the present invention had no Pt condensation such as that which occurred in Sample No. C1 shown in FIG. 5, and this fact suggests the high resistance to Pb poisoning of the electrode of the present invention.

EXAMPLE 1

The following description should be read with reference to FIGS. 1 to 3.

A solid electrolyte body made of zirconia was formed into a hollow tube 1 about 7 mm in diameter, 30 mm long and 1 mm in wall thickness. On the outside surface of the zirconia tube 1 that was exposed to a gas of interest was formed a first electrode metal layer which was composed of a Pt layer (1 micron) deposited by plating and an overlaying Pt-10% Rh layer (0.2 micron) deposited by sputtering. The proportion of Rh in the first electrode metal layer was 1.7%. On the other (inside) surface of the zirconia tube, a second electrode 22 was plated from platinum in a thickness of 3,000 Å. The hollow zirconia tube with the first electrode metal layer and the second electrode was heated in oxygen gas at 800° C. for 1 hr, then heated in hydrogen gas at 200° C. for 1 hr. As a result of these oxidation and reduction treatments, a dual layered first electrode 21 formed consisting of a platinum layer 211 overlaid with a rhodium-concentrated layer 212 having a thickness of 200 Å.

A protective layer 3 (100 microns) made of MgO.Al$_2$O$_3$ spinel was formed on the surface of the first electrode 21 by plasma spraying. By these procedures, an oxygen sensor in accordance with the present invention was fabricated (Sample No. 3).

Two comparative sensors (Samples Nos. C3 and C4) were fabricated as above, except that the first electrode 21 of C3 was made of a Pt layer that was neither oxidized nor reduced, and that the first electrode of C4 was made of a layer of Pt-10% Rh alloy that was neither oxidized nor reduced.

Each of the three sensor samples was mounted in a holder 4 and connected to a lead wire 5 for conducting a test to evaluate the response characteristics of each sensor. In the test, the temperature of the sensor tip was set at 450° C. and the response time from (fuel-rich to fuel-lean) in terms of voltage change upon switching the air excess ratio of a model gas from 0.9 (reducing atmosphere) to 1.1 (oxidizing atmosphere) was measured.

The test results are shown in Table 2 below together with the materials of the first electrode 21 and the indication of whether they were subjected to oxidation/reduction treatments. A practically feasible oxygen sensor should not have a response time longer than 260 msec.

As Table 2 shows, the oxygen sensor in accordance with the present invention has a much faster response than the comparative sensors and its response time is well suited to practical applications.

TABLE 2

| Sample No. | First electrode layer composition | thickness (microns) | Oxidation reduction treatments | Response time (msec) |
|---|---|---|---|---|
| 3 | Pt-10% Rh | 1.2 | yes | 230 |
| C3 | Pt | 1.2 | no | 350 |
| C4 | Pt-10% Rh | 1.2 | no | 310 |

EXAMPLE 2

An oxygen sensor (Sample No. 4) in accordance with the present invention was fabricated as in Example 1, except that the first electrode 21 was made of a plated Pt-5% Rh layer 1 micron thick that was later subjected to oxidation and reduction treatments. The first electrode of Sample No. 4 had a dual structure consisting of a Pt layer and an overlaying Rh layer 500 Å thick.

Comparative sensor Sample No. C5, was fabricated as above, except that the first electrode was made of a Pt layer 1 micron thick that was subjected to neither oxidation nor reduction treatment.

The two sensors were tested for their durability by the following procedure. Each of the sensors as mounted in a holder 4 and connected to a lead wire 5 attached to an exhaust pipe leading from an engine of 2,000 cc displacement and with six cylinders that was running at 3,600 rpm. After exposure to the exhaust gas at 500° C. for two different periods, 100 and 200 hrs, the response time (from fuel-rich to fuel-lean) of each sensor was determined by the same method as used in Example 1. The results are shown in Table 3 below.

As one can see from Table 3, the oxygen sensor in accordance with the present invention had a shorter response time than the comparative sample and exhibited a greater durability since the response did not appreciably slow down as the exposure of the sensor to exhaust gas was prolonged.

TABLE 3

| Sample No. | First electrode layer composition | thickness (microns) | Response time (msec) Initial | 100 hrs | 200 hrs |
|---|---|---|---|---|---|
| 4 | Pt-5% Rh | 1 | 210 | 230 | 240 |
| C5 | Pt | 1 | 280 | 340 | 460 |

We claim:

1. In a process for producing an oxygen sensor having a first electrode formed on that side of a solid electrolyte body which is faced to a gas to be detected and a second electrode formed on the other side of the solid electrolyte body, the improvement comprising the steps of:

forming a first electrode metal layer made of a mixture of platinum and at least one rhodium and palladium directly on that surface of the solid electrolyte body where the first electrode is to be formed, and subjecting the first electrode metal layer to oxidation and then to reduction to allow said rhodium and/or palladium in said mixture to be concentrated and overlaid on said platinum to produce a dual structure in the first electrode of a platinum layer overlaid with a layer of concentrated rhodium and/or palladium.

2. A process according to claim 1, wherein a protective layer is formed on the side of said first electrode exposed to the gas to be detected.

3. A process according to claim 1, wherein said solid electrolyte body is made of at least one material selected from the group consisting of zirconia, thoria, ceria, ceria-lanthania, ceria-thoria-lanthania, and bismuth oxide.

4. A process according to claim 1, wherein said solid electrolyte body is comprised of zirconia doped with an oxide of at least one element selected from the group consisting of yttrium, calcium, magnesium, ytterbium, cerium, scandium, lanthanum, and strontium.

5. A process according to claim 1, wherein said first electrode metal layer is formed by one of spraying, print firing, sputtering, evaporation and plating.

6. A process according to claim 1, wherein the amount of rhodium and/or palladium to be incorporated in said first electrode is in the range of 0.1 to 50 wt% of the total weight of said metal layer.

7. A process according to claim 1, wherein the heating temperature is in the range of 600° to 900° C. and the duration time is in the range of 5 minutes to 3 hours in said oxidation treatment.

8. A process according to claim 1, wherein the heating temperature is in the range of 100° to 200° C. and the duration time is in the range of 5 minutes to 1 hour in said reducing treatment.

9. A process according to claim 1, wherein said first electrode metal layer is heated in oxygen gas and then heated in hydrogen gas to form the first electrode including the rhodium and/or palladium layer with a thickness of 10 to 5000 Å.

* * * * *